US008753484B2

(12) United States Patent
Tan et al.

(10) Patent No.: US 8,753,484 B2
(45) Date of Patent: *Jun. 17, 2014

(54) LIGNO CELLULOSIC MATERIALS AND THE PRODUCTS MADE THEREFROM

(75) Inventors: Zheng Tan, Altanta, GA (US); Damaris Lorenzoni, Venda Nova do Imigrante (BR); Gopal Goyal, Mason, OH (US); Sen Yang, Nanuet, NY (US)

(73) Assignee: International Paper Company, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/611,131

(22) Filed: Sep. 12, 2012

(65) Prior Publication Data

US 2013/0066291 A1  Mar. 14, 2013

Related U.S. Application Data

(60) Continuation of application No. 13/204,986, filed on Aug. 8, 2011, now Pat. No. 8,282,774, which is a division of application No. 11/417,268, filed on May 2, 2006, now Pat. No. 8,007,635.

(60) Provisional application No. 60/760,073, filed on Jan. 19, 2006, provisional application No. 60/676,828, filed on May 2, 2005.

(51) Int. Cl.
  *D21C 9/16* (2006.01)
(52) U.S. Cl.
  CPC ..................... *D21C 9/163* (2013.01)
  USPC ............................ 162/231; 162/100; 604/378
(58) Field of Classification Search
  CPC ...................................... D21C 9/163
  USPC .................................. 162/100, 231; 604/378
  See application file for complete search history.

(56) References Cited

U.S. PATENT DOCUMENTS

| | | | |
|---|---|---|---|
| 1,298,552 A | 3/1919 | Ornstein | |
| 1,298,553 A | 3/1919 | Ornstein | |
| 1,298,554 A | 3/1919 | Ornstein | |
| 1,860,431 A | 5/1932 | Richter | |
| 2,178,696 A | 11/1939 | Muskat et al. | |
| 2,212,338 A | 8/1940 | Bown | |
| 2,368,527 A | 1/1945 | Edelstein | |
| 2,512,338 A | 6/1950 | Klug et al. | |
| 2,975,169 A | 3/1961 | Cranford et al. | |
| 3,308,012 A | 3/1967 | Tobar | |
| 3,707,148 A | 12/1972 | Bryce | |
| 4,022,965 A | 5/1977 | Goheen et al. | |
| 4,222,819 A | 9/1980 | Fossum et al. | |
| 4,270,976 A | 6/1981 | Sandstrom et al. | |
| 4,410,397 A | 10/1983 | Kempf | |
| 4,427,490 A | 1/1984 | Eckert | |
| 4,444,621 A | 4/1984 | Lindahl | |
| 4,454,005 A | 6/1984 | Stofko | |
| 4,470,212 A | 9/1984 | Stafford et al. | |
| 4,599,138 A | 7/1986 | Lindahl | |
| 4,614,646 A | 9/1986 | Christiansen | |
| 4,661,205 A | 4/1987 | Ow et al. | |
| 4,756,799 A | 7/1988 | Bengtsson et al. | |
| 4,783,239 A | 11/1988 | Rich | |
| 4,869,783 A | 9/1989 | Prusas et al. | |
| 4,875,974 A | 10/1989 | Rich | |
| 4,889,595 A | 12/1989 | Herron et al. | |
| 5,002,635 A | 3/1991 | Gentile, Jr. et al. | |
| 5,296,099 A | 3/1994 | Griggs et al. | |
| 5,300,358 A | 4/1994 | Evers | |
| 5,383,964 A | 1/1995 | Suc et al. | |
| 5,447,602 A | 9/1995 | Sajbel et al. | |
| 5,460,924 A | 10/1995 | Buchanan et al. | |
| 5,529,662 A | 6/1996 | Tan et al. | |
| 5,536,625 A | 7/1996 | Buchanan et al. | |
| 5,552,019 A | 9/1996 | Weinstock et al. | |
| 5,607,546 A | 3/1997 | Hoglund et al. | |
| 5,766,159 A | 6/1998 | Martin et al. | |
| 6,063,982 A | 5/2000 | Mertin et al. | |
| 6,214,164 B1 | 4/2001 | Rantala | |
| 6,258,207 B1 | 7/2001 | Pan | |
| 6,302,997 B1 | 10/2001 | Hurter et al. | |
| 6,306,253 B2 | 10/2001 | Henricson | |
| 6,368,456 B1 | 4/2002 | Cimecioglu et al. | |
| 6,379,494 B1 | 4/2002 | Jewell et al. | |
| 6,398,908 B1 | 6/2002 | Hermansson et al. | |

(Continued)

FOREIGN PATENT DOCUMENTS

| | | |
|---|---|---|
| CA | 1129161 | 8/1982 |
| CA | 1190360 | 7/1985 |

(Continued)

OTHER PUBLICATIONS

Effect and Control of Transition Metal Ions During Paracid Bleaching, South China University of Technology, Guangzhou, 510640.
Qian, Y; Goodell, B.; Genco, J.M., (2002): Journal of Wood Chemistry and Technology, vol. 22, No. 4, pp. 267-284, 2002.
G.A. Smook "Handbook for Pulp Paper Technologist," 1992, Angus Wilde Publications, 2nd Edition, pp. 194-208.

(Continued)

*Primary Examiner* — Anthony Calandra
(74) *Attorney, Agent, or Firm* — Thomas W. Barnes, III

(57) ABSTRACT

A process comprising treating a lignocellulosic material preferably pulp in the presence of a transition metal catalyst with a oxidizing agent selected from a group consisting of hydrogen peroxide, hypochlorite, hypochlorous acid and any combination thereof to form a treated lignocellulosic material having a viscosity equal to or less than about 17 cp and having reducing functional groups selected from the group consisting of aldehyde and aldehyde type functional groups at the C6 and C1 positions but predominating at the C1 position.

15 Claims, No Drawings

(56) References Cited

U.S. PATENT DOCUMENTS

| | | |
|---|---|---|
| 6,436,238 B1 | 8/2002 | Pitkanen et al. |
| 6,458,245 B1 | 10/2002 | Hoglund et al. |
| 6,514,380 B1 | 2/2003 | Laine et al. |
| 6,562,195 B2 | 5/2003 | Cimecioglu et al. |
| 6,605,350 B1 | 8/2003 | Sealey et al. |
| 6,632,328 B2 | 10/2003 | Wan et al. |
| 6,635,755 B1 | 10/2003 | Jaschinski et al. |
| 6,695,950 B1 | 2/2004 | Cimeciouglu et al. |
| 6,699,358 B1 | 3/2004 | Evans et al. |
| 6,743,332 B2 | 6/2004 | Haynes et al. |
| 6,765,042 B1 | 7/2004 | Thornton et al. |
| 6,770,168 B1 | 8/2004 | Stigsson |
| 6,773,552 B1 | 8/2004 | Albert et al. |
| 6,824,645 B2 | 11/2004 | Jaschinski et al. |
| 6,852,904 B2 | 2/2005 | Sun et al. |
| 6,881,299 B2 | 4/2005 | Parrish et al. |
| 6,923,889 B2 | 8/2005 | Huuskonen et al. |
| 7,094,317 B2 | 8/2006 | Lundberg et al. |
| 7,279,071 B2 | 10/2007 | Williams et al. |
| 7,326,317 B2 | 2/2008 | Westermark et al. |
| 7,520,958 B2 | 4/2009 | Tan et al. |
| 8,262,850 B2 | 9/2012 | Tan et al. |
| 8,282,774 B2 | 10/2012 | Tan et al. |
| 2001/0028955 A1 | 10/2001 | Luo et al. |
| 2001/0050153 A1 | 12/2001 | Wajer et al. |
| 2002/0005262 A1 | 1/2002 | Cimecioglu et al. |
| 2002/0144796 A1 | 10/2002 | Wan et al. |
| 2002/0165110 A1 | 11/2002 | Reinhardt et al. |
| 2003/0019596 A1 | 1/2003 | Ragauskas et al. |
| 2003/0026828 A1 | 2/2003 | Besemer et al. |
| 2004/0154761 A1 | 8/2004 | Duggirala et al. |
| 2004/0154765 A1 | 8/2004 | Huuskonen et al. |
| 2005/0061455 A1 | 3/2005 | Tan et al. |
| 2006/0144535 A1 | 7/2006 | Nguyen et al. |
| 2006/0260773 A1 | 11/2006 | Tan et al. |
| 2007/0000627 A1 | 1/2007 | Tan et al. |
| 2007/0051481 A1 | 3/2007 | Tan et al. |
| 2007/0119556 A1 | 5/2007 | Tan et al. |
| 2007/0143932 A1 | 6/2007 | Buchert et al. |
| 2007/0163735 A1 | 7/2007 | Buchert et al. |
| 2008/0294132 A1 | 11/2008 | Tan et al. |
| 2009/0054863 A1 | 2/2009 | Tan et al. |
| 2009/0165968 A1 | 7/2009 | Tan et al. |
| 2013/0092336 A1 | 4/2013 | Tan et al. |
| 2013/0098571 A1 | 4/2013 | Tan et al. |
| 2013/0126109 A1 | 5/2013 | Wang |
| 2013/0126111 A1 | 5/2013 | Hage et al. |
| 2013/0197461 A1 | 8/2013 | Nonni et al. |
| 2013/0206349 A1 | 8/2013 | Nonni et al. |
| 2013/0248131 A1 | 9/2013 | Nonni et al. |
| 2014/0000824 A9 | 1/2014 | Hage et al. |
| 2014/0000825 A1 | 1/2014 | Tan et al. |

FOREIGN PATENT DOCUMENTS

| | | |
|---|---|---|
| DE | 10123665 | 11/2002 |
| EP | 1077285 | 2/2001 |
| EP | 1156065 | 11/2001 |
| EP | 1245722 | 10/2002 |
| EP | 1862587 | 12/2007 |
| FR | 2688787 | 9/1993 |
| GB | 555985 | 9/1943 |
| JP | 58054089 | 3/1983 |
| JP | 2001115389 | 4/2001 |
| JP | 2003026701 | 1/2003 |
| RU | 2003131266 | 5/2005 |
| WO | 9535408 | 12/1995 |
| WO | 9722749 | 6/1997 |
| WO | 02095129 | 11/2002 |
| WO | 03042451 | 5/2003 |
| WO | 03051410 | 6/2003 |
| WO | 2005028744 | 3/2005 |
| WO | 2006119392 | 11/2006 |
| WO | 2006127880 | 11/2006 |

OTHER PUBLICATIONS

Sun et al. Abstract of "The effect of metal ions on the reaction of hydrogen peroxide with Kraft lignin model compounds;" 1999, Can. J. Chem, vol. 77 (5-6, pp. 667-675).

Leporini et al. In "Hydrogen Peroxide in Chemical Pulp Bleaching—an overview-;" 2002; Congreso Iberoamericano de Invesigacion en cellulosa y Papel; CIADICYP; pp. 1-27.

Rahmawati et al. In "Pulp bleaching by hydrogen peroxide activated with copper 2,2_-dipyridylamine and 4-aminopyridine complexes;" 2005, Chemical Engineering Journal, vol. 112, pp. 167-171.

Ruuttunen et al. In "Concomitant Usage of Transition Metal Polyanions as Catalysts in Oxygen Delignification: Laboratory Bleaching Trials;" 2006, Appita Journal, pp. 1-14.

Kubelka et al. in "Delignification with Acidic Hydrogen Peroxide Activated by Molybdate", May 1992, Journal of Pulp and Paper Science, vol. 18, No. 3, pp. J108-J114.

Zeronian et al., Bleaching of cellulose by hydrogen peroxide, 1995, Cellulose, pp. 265-272.

Lenntech, http://www.lentech.com/Fenton-reaction.htm [downloaded from www.archive.org], Jun. 28, 2003 [downloaded on Jun. 19, 2008], whole document.

Shenai, Studies in Chemically Modified Celluloses. IX. Oxidation of Cellulose in the Presence of Chelating Agents, 1976, Journal of Applied Polymer Science, vol. 20, pp. 385-391.

Smook, Handbook for Pulp and Paper Technologists, 1992, Angus Wilde Publications, 2nd edition, p. 228.

Gullichsen et al., Chemical Pulping 6A, 1999, Fapet Oy, p. A207 and A653.

Fibersource, Cellulose [downloaded online from http://www.fibersource.com/F-TUTOR/cellulose.htm], downloaded on Jan. 16, 2010, Fibersource, pp. 1-4.

Burgess, Relationship Between Colour Production in Cellulose and the Chemical Changes Brought About by Bleaching, 1982, The American Institute for Conservation, vol. 1, pp. 1-7.

LIGNO CELLULOSIC MATERIALS AND THE PRODUCTS MADE THEREFROM

RELATED APPLICATION(S)

This application is a continuation of U.S. patent application Ser. No. 13/204,986, filed Aug. 8, 2011, now U.S. Pat. No. 8,282,774, which is a division of U.S. patent application Ser. No. 11/417,268, filed May 2, 2006, now U.S. Pat. No. 8,007,635, which claims benefit from U.S. patent application Ser. No. 60/676,828, filed May 2, 2005; and U.S. patent application Ser. No. 60/760,073, filed Jan. 19, 2006.

BACKGROUND OF THE INVENTION

Cellulose pulps have been used in a variety of personal care or medical care absorbent products, for instance, diaper fluff or incontinence articles. One important issue of these applications is the odor caused by the body fluids. In the case of diaper fluff, ammonia odor from the urine is the major concern. For other applications, malodorous issue may be caused by other nitrogen-containing or sulfur-containing substances.

From literature, it is found that a variety of additives have been used to absorb the odors. See for example, U.S. Pat. Nos. 6,765,042 and 6,852,904, and US Patent Application No. 00268281 A 1.

SUMMARY OF THE INVENTION

One aspect of this invention relates to a process comprising treating a lignocellulosic material, preferably in fibrous or particulate form and more preferably a hardwood, a softwood pulp or a combination thereof, in the presence of a transition metal catalyst with an oxidizing agent selected from a group consisting of hydrogen peroxide, hypochlorite, chlorine dioxide, hypochlorous acid and any combination thereof to form a treated lignocellulosic material having a viscosity equal to or less than about 17 cps and preferably having reducing functional groups selected from the group consisting of aldehyde and aldehyde type functional groups such as hemiacetals that predominate at the C1 position. As used herein the term "lignocellulosic material" means an organic polymeric or oligomeric material having substituted or unsubstituted carbohydrate (such as glucose, mannose, xylose, arabinose, galactose and the like) units as for example cellulose, hemicellulose and polysaccharides. As used herein, the term "predominate" means more than 50% based on the total weight of reducing functional groups. In the preferred embodiments of the invention, the treated lignocellulosic material preferably has a copper number of more than about 0.5 and/or a carboxyl content of more than about 3.5 meq/100 gram.

Another aspect of the invention relates to a treated lignocellulosic material having a viscosity equal to or less than about 17 cps. The material preferably has reducing end groups selected from the group consisting of aldehyde and aldehyde type functional groups such as hemiacetals that predominate at the C1 position i.e., at least about 50% based on the total number of aldehyde and aldehyde type functional groups contained in the treated lignocellulosic material. The amount of aldehyde and aldehyde type functional groups at the C1 position is preferably greater than about 75%, more preferably equal to or greater than about 80% and most preferably equal to or greater than about 90% based on the total amount of aldehyde and aldehyde type functional groups contained in the treated lignocellulosic material. In the embodiment of choice, the amount of aldehyde and aldehyde type functional groups are at the C1 position equal to about 95%. In the preferred embodiments of the invention, the treated lignocellulosic material preferably has a copper number of more than about 4 and/or a carboxyl content of more than about 4.5 meq/100 grams.

The treated lignocellulosic materials of this invention exhibit one or more beneficial properties. For example, the materials may exhibit odor control properties. While we do not wish to be bound by any theory it is believed that some materials control odor by complexing with odoriferous materials as for example ammonia from urine and/or by inhibiting the growth of bacteria that convert urea into ammonia. The odor control characteristics of these lignocellulosic materials especially pulp makes them especially useful in the construction of absorbent personal hygiene articles such as diapers, feminine hygiene articles, adult incontinency products and the like, with or without SAP. Certain embodiments of the treated lignocellulosic material of this invention exhibit good wet strength and/or drainage properties. Certain other embodiments of the invention where the ligno cellulosic material is pulp surprisingly still maintain most of the paper mechanical properties unchanged compared with the untreated pulp, except with the possible exception of tear strength.

Yet another aspect of this invention relates to a personal hygiene article for absorbing fluids, the article comprising:

at least one fluid permeable top sheet layer and at least one substantially fluid impermeable back sheet layer; and an absorbent sub layer material interposed between the top sheet layer and the back sheet layer, the sub layer material comprising the treated lignocellulosic material of this invention.

Still another aspect of this invention relates to a method for making an absorbent composite useful for personal hygiene articles which comprises:

dry shredding the treated lignocellulosic material of this invention to form an absorbent sub layer material comprised of fluffed base-treated wood pulp;

providing at least one fluid permeable top sheet layer and at least one substantially fluid impermeable back sheet layer; and interposing the sub layer material between the top sheet layer and back sheet layer.

Still another aspect of this invention relates to a paper or paperboard making process which comprises the steps of:

(a) forming an aqueous paper making stock furnish comprising pulp having a viscosity equal to or less than about 17 cp and having reducing end groups selected from the group consisting of aldehyde and aldehyde type functional groups at the C6 and C1 positions but predominating at the C1 position;

(b) depositing said furnish on a forming wire of a paper making machine to form a wet paper web; and (c) drying said wet paper or paperboard web to form a dried paper or paperboard.

Yet another aspect of this invention relates to a paper or paperboard comprising pulp having a viscosity equal to or less than about 17 cp and having reducing end groups selected from the group consisting of aldehyde and aldehyde type functional groups at the C6 and C1 positions but predominating at the C1 position.

DETAIL DESCRIPTION OF THE INVENTION

One aspect of this invention relates to a process comprising treating a lignocellulosic material, preferably wood pulp, in the presence of a transition metal catalyst with an oxidizing agent selected from a group consisting of hydrogen peroxide, chlorine dioxide, hypochlorite, hypochlorous acid and any combination thereof.

The lignocellulosic material can be in fibrous or particulate form as for example pulp fibers, fines and other pulp fragments; hemicellulose, starch and polysaccharide particles and powders. The lignocellulosic material can also be in solution as for examples solutions of cellulose derivatives such as carboxymethyl cellulose, hydroxypropyl cellulose and the like.

The type of lignocellulosic material used in the process of this invention is not critical and any such material can be used. For example, useful lignocellulosic materials include those derived from known sources of such materials as for example plants. Illustrative of useful lignocellulosic materials are polysaccharides such as starches. Useful starches for the practice of this invention are naturally occurring carbohydrates synthesized in corn, tapioca, potato and other plants by polymerization of dextrose units. All such starches and modified forms thereof such as starch acetates, starch esters, starch ethers, starch phosphates, starch xanthates, anionic starches, cationic starches and the like which can be derived by reacting the starch with a suitable chemical or enzymatic reagent can be used in the practice of this invention. Useful polysaccharides can be hemicellose extracted from wood porior to pulping or extracted from the pulp fibers after pulping and can be corn fiber kernels which can be enriched with xylanes, celluloses, starches or a combination of any two or more thereof. Also Illustrative of lignocellulosic materials for use in the practice of the process of this invention are pulp fibers used in the formation of tissues, towels, diapers, feminine hygiene and adult incontinence products and used to make other types of pulp products, paper and paperboard. Such pulp fibers include those derived from hardwood trees, softwood trees, or a combination of hardwood and softwood trees prepared for use in a papermaking furnish by any known suitable digestion, refining, and bleaching operations as for example known mechanical, thermo mechanical, chemical and semi chemical, etc., pulping and other well known pulping processes. The term "hardwood pulps" as used herein refers to fibrous pulp derived from the woody substance of deciduous trees (angiosperms), whereas "softwood pulps" are fibrous pulps derived from the woody substance of coniferous trees (gymnosperms). Useful pulp fibers may be provided from non-woody herbaceous plants including, but not limited to, kenaf, hemp, jute, flax, sisal, or abaca although legal restrictions and other considerations may make the utilization of hemp and other fiber sources impractical or impossible. Either bleached or unbleached pulp fiber as for example unbleached kraft and bleached kraft pulp, or recycled pulp may be utilized in the process of this invention. The pulp may have been subjected to any treatment history that is normal in pulping and bleaching or may be intentionally modified as for example by controlled prehydrolysis or caustic extraction of chips before kraft pulping, acid or enzyme (cellulases or hemicellulases) hydrolysis of kraft pulps, "cold-soda" treatment of pulp (up to mercerizing strength).

Preferred lignocellulosic materials are hardwood pulp, softwood pulp or a combination thereof. More preferred lignocellulosic materials are kraft hardwood pulps, softwood pulp or a combination thereof. Most preferred lignocellulosic materials are bleached kraft hardwood pulps, softwood pulps or a combination thereof, especially bleached kraft softwood pulps.

Transition metal catalyst used in the practice of this invention may vary widely and any transition metal can be used. Illustrative of such metals are Cu, Fe, Zn, Co, Ni, Mn, V, Mo, W, Zr, Ce, Cr and any combination thereof. The metals are preferably used in the form of salts, preferably water soluble metal salts. Preferred metal salts include halide, sulfate, nitrate and phosphate and carbonate metal salts and combinations thereof. Most preferred metal salts are Cu (Cu+ and Cu 2+, Fe (Fe 3+, Fe 2+) and Zn (Zn2+) metal salts with Cu and Fe metal salts being those of choice.

The amount of metal catalyst used in the process of this invention may vary widely and any amount sufficient to form the desired treated lignocellulosic product can be used. The amount of metal catalyst is usually at least about 0.005% by wgt of the dried lignocellulosic material even though higher or lower amounts may be used. The amount of metal catalyst is preferably from about 0.005 to about 1% by wgt of the dried lignocellulosic material, more preferably about 0.01 to about 0.5% by wgt of the dried lignocellulosic material and most preferably about 0.01 to about 0.1% by wgt of the dried lignocellulosic material.

Oxidizing agent for use in the process are selected from a group consisting of hydrogen peroxide, chlorine dioxide, hypochlorite, hypochlorous acid and any combination thereof. The preferred oxidizing agents are hydrogen peroxide and hypochlorite and the most preferred oxidizing agent is hydrogen peroxide.

The amount of the oxidizing agent may vary widely and any amount sufficient to form the desired treated lignocellulosic product can be used. The amount of the oxidizing agent is usually at least about 0.1% by wgt of the dried lignocellulosic material although lower amounts may used if effective to provide the desired ligno cellulosic material. The amount of the oxidizing agent is preferably from about 0.1 to about 10% by wgt of the dried lignocellulosic material, more preferably about 0.1 to about 5% by wgt of the dried lignocellulosic material and most preferably about 0.5 to about 5% by wgt of the dried lignocellulosic material.

Treatment temperatures may vary widely and any temperature sufficient to form the desired treated lignocellulosic product can be used. The treatment temperature is usually at least about 20° C. although lower temperatures may be used if effective to provide the desired ligno cellulosic material. The treatment temperature is preferably from about 20° C. to about 120° C., more preferably from about 40° C. to about 120° C. and most preferably from about 40° C. to about 90° C., with a treatment temperature of from about 60° C. to about 90° C. being the treatment temperature in the embodiments of choice.

Treatment pH may vary widely and any temperature sufficient to form the desired treated lignocellulosic product can be used. The treatment pH is usually between about 1 and about 9 although lower or higher pHs may be used if effective to provide the desired ligno cellulosic material. The treatment pH is preferably from about 2 to about 8, more preferably from about 2 to about 7 and most preferably from about 2 to about 6.

Treatment times may vary widely and any time sufficient to form the desired treated lignocellulosic product can be used. The treatment time is usually at least about 5 minutes although longer treatment times may be used if effective to provide the desired ligno cellulosic material. The treatment time is preferably from about 5 minutes to about 20 hours, more preferably 15 minutes to about 10 hours and most preferably from about 30 minutes to about 4 hours.

Optionally the process of this invention can be carried out in the presence of UV radiation preferably when peroxide is used as the oxidizing agent. The UV treatment has the advantage of being more effective at lower temperatures such as room temperature (or ambient temperature) without need for heating equipment and can be used to widening the pH effective range. For example, the process can be effectively carried in the presence of UV radiation at ambient temperature (or without heating), at neutral pH in a very short time of from a few seconds to 1 hour, depending on UV lamp power and fiber mixing conditions. The UV lamp used in the process, preferably is a high intensity lamp, such as medium pressure mercury arc lamp or its variants, pulsed Xenon flash lamps, or excimer lamps. It is most preferable to use the medium pressure mercury arc lamp which is low cost and readily available from commercial sources. The UV lamps, which are inserted in quartz sleeves, can be inserted (submerged) into the pulp suspension for irradiation. Sometimes, it may be more advantageous to put UV lamps above the mixing suspension of the lignocellulosic material. For this type of UV irradiation, both mercury arc lamps and electrode-less powered lamps (such as from Fusion UV company) can be used. It is preferred that the pulp fibers are fully mixed and well stirred during reaction since UV penetration in water is very low and most chemical action has to come from UV decomposing the peroxide in water solutions. The UV treatment can be done with addition of catalyst to the UV-peroxide system as well. Useful catalysts may vary widely and any conventional UV catalyst can be used as for example water-soluble metal salts such as iron salts or copper salts used in the process; micro- or nano-particulate titanium dioxide or zinc oxide photo-catalysts; azo based organic catalyst, such as water-soluble 4,4'-azobis (4-cyanovaleric acid), 2,2'-azobis (2-methylpropionamidine dihydrochloride, AIBN or Dupont Vazo catalyst 88; and 2,2, 6,6-tetramethyl-1-piperidinyloxy (TEMPO).

The process can be conducted batch wise, continuously or semi continuously. The process of this invention can also be practiced as part of a pulping process as a process step at the end of a mechanical, semi-chemical or chemical pulping process or as a part of a bleaching process as a process step at the end of the bleaching process. The process can also be used to treat market paper making pulp or fluff pulp as for example by re-slushing market paper making pulp or fluff pulp in a hydro-pulper or like-device. The treatment in the hydro-pulper or like-device has the flexibility of adjusting conditions. For instance, the treatment started at acidic pH and after some appropriate period of time adjusting to alkaline pH by the addition of caustic and continuing the reaction at higher pH. This combined acidic-alkaline treatment can be used to change the ratio of carboxyl vs. carbonyl groups in the treated lignocellulosic material.

The treated lignocellulosic material formed by the process of this invention has a viscosity less than 17 cps as measured by the procedure of TAPPI T-230. This is in contrast to the viscosity of untreated pulp which is usually greater than about 17 cps. The treated lignocellulosic material preferably has a viscosity of equal to or less than about 15 cps, more preferably equal to or less than about 12 or equal to or less than about 10 cps and most preferably from about 1 to about 10 cps. In the embodiments of choice, the treated lignocellulosic material formed by the process of this invention has a viscosity of from about 2 to about 7 cps. It is believed that the lowered pulp viscosity indicates a greater amount of reducing functional groups at the C1 position at the end of the molecular or oligomeric chains forming the treated lignocellulosic material. While we do not wish to be bound by any theory it is believed that this would provide more binding sites for some transitional metals, for instance copper and some others and that the end reducing functional groups act as the other functional sites, in addition to other oxidized groups on the polysaccharide units. It may sometimes be advantageous to increase the amount of end reducing functional groups ends provided by this invention be further treating the treated lignocellulosic material in an acid hydrolysis or enzymatic hydrolysis step which is believed will further increase the odor control properties of the treated lignocellulosic material.

The treated lignocellulosic material formed by the process of this invention preferably has a degree of polymerization of less than about 1200. In these preferred embodiments of the invention the treated lignocellulosic material more preferably has a degree of polymerization equal to or less than about 1000 and most preferably equal to or less than about 900. In the embodiments of choice of these preferred embodiments of the invention, the treated lignocellulosic material formed by the process of this invention has degree of polymerization of from about 100 to about 800 or from about 200 to about 600. In a preferred embodiment of the invention, the treated lignocellulosic material formed by the process of this invention has reducing groups selected from the group consisting of aldehyde and aldehyde type functional groups such as hemiacetals that predominate at the C1 position which results when the lignocellulosic chain is oxidatively cut during the process to reduce the degree of polymerization and the viscosity of the treated pulp. The amount of such end groups can be determined by the procedures set forth in U.S. Pat. No. 6,635,755 and references cited therein and other methods known to those of ordinary skill in the art. According to the invention it is possible that the reducing functional groups can isomerize into groups other than of aldehyde and aldehyde type functional groups. Because of the randomness of the oxidation process, it is also possible that aldehyde or aldehyde type function groups may be present at the C6 position and/or ketone functions may be present at the C3 and/or C4 positions all though at a lesser extent. Preferably the amount of aldehyde and aldehyde type functional groups reducing groups present at the C1 position is greater than about 75% based on the total amount of aldehyde and aldehyde type functional groups. The amount of aldehyde and aldehyde type reducing functional groups present at the C1 position is more preferably equal to or greater than about 80% and most preferably equal to or greater than about 90% on the aforementioned basis. In the embodiment of choice, the amount of aldehyde and aldehyde type reducing functional groups at the C1 position equal to about 95% based on the total amount of aldehyde and aldehyde type reducing functional groups.

In the preferred embodiments of the invention, the treated lignocellulosic material formed by the process of this invention has a copper number equal to or greater than about 3. The copper number is measured by the following procedure of Tappi T-430 cm-99. The treated lignocellulosic material preferably has a copper number equal to or greater than about 4.4, more preferably equal to or greater than about 5 and most preferably equal to or greater than about 5.5.

In the preferred embodiments of the invention, the treated lignocellulosic material formed by the process of this invention has carboxy number equal to or more than about 3.5 meq/100 grams of oven dried treated material. The carboxy number is measured by the following procedure Tappi T-237 cm-98. The treated lignocellulosic material preferably has a carboxyl number of above 4, more preferably above 5 and most preferably above 5.5 meq/100 g.

In a preferred embodiment of this invention, the treated lignocellulosic material formed by the process of this invention has odor control properties as measured by the ability to bind or complex with ammonia and by its bacterial inhibition activity. The ability of the material to complex with ammonia is determined by the following test: A Kamas lab hammermill equipped with a forming funnel was used to form the fiberized pulp into 50 cm2, 3.00 gram pads formed from the lignocellulosic material. The pads were placed inside a jar that is sealed with a lid containing a septum as a sampling port. The pads were dosed with 500 micro-liter of a 0.6% ammonia solution through a gas tight syringe having a needle of sufficient length to touch the pad surface. After an equilibration period of 45 minutes, 1 qt headspace gas was sampled through the port using a calibrated hand pump and an ammonia indicator tube (i.e., Drager tube sampling system), withdrawing the sample through a needle adapter attached to the tube. In the preferred embodiments of the invention the amount of ammonia adsorbed by the treated the lignocellulosic material is 50% higher, preferably 60% higher and more preferably 80% higher than the amount of ammonia adsorbed by same or substantially same lignocellulosic material prior to treatment in the process of this invention. In the embodiments of choice, the amount of ammonia absorbed is above 90% higher than the untreated pulp.

The bacterial inhibition property of the treated lignocellulosic is determined using the test organisms *Corynebacterium ammoniagenes*, ATCC 6871 propagated in Urea Medium (I-144C) and grown at 37±2° C. for 2-3 days in a shaker flask and *Escherichia coli* ATCC 11229 propagated in Tryptic Soy Broth (I-053B) and grown at 37±2° C. for 18-24 hours in a shaker flask. The organisms were assigned unique codes to provide for correct generation of data. ASTM Method E 2180-01 was used to determine the microbial load and percent reduction, $Log_{10}$ reduction or $Log_{10}$ increase in numbers on the test substance against the test organism(s) modified as follows:

The 15×100 mm sterile Petri dish containing the sample ([50 mm] 2" diameter) will be placed inside a larger Petri dish containing 10 mL of water to increase the humidity and prevent drying during the exposure period.

1) The samples will be hydrated, prior to inoculation with 0.5 mL of the test culture.
2) No "Agar Slurry" will be used.
3) The samples will be evaluated in duplicate.
4) The samples will be held at 35±2° C. in a humidified chamber for 3 and 8 hour exposure periods (±10 minutes).
5) The neutralizer will be 50-mL volumes of Tryptic Soy Broth with 10% Tween 80, 3% Lecithin, and 0.5% Sodium Thiosulfate, and 0.1% Histidine, pH 7.2±0.1 (I-148) in sterile 2 oz. jars.
6) Sonicate the sample in neutralizer for 1 minute followed by vortexing for 1 minute prior to diluting.
7) Serial dilutions will be prepared to $10^{-5}$ through 9-mL volumes of 2× Difco Neutralizing Buffer. Dilutions will be prepared to $10^{-6}$ for the Control with plating in duplicate by the Spread Plate Method using Urea Agar (I-145C) and Mac Conkey Agar (I-090B). The undiluted sample in neutralizer ($10^0$ dilution [50 mL]) will be plated by spreading 1 mL across 3 plates.
8) Incubation will be at 35±2° C. for 3 days for Urea Agar and at 35±2° C. for 18-24 hours for Mac Conkey Agar.
9) Neutralizer effectiveness will be conducted concurrently with testing using *E. coli* as the test organism.

The validity of the results obtained by the above procedure relies on a demonstration that the test substance(s) does not, under the conditions of the test, inhibit the multiplication of viable organisms that may be present; and, that the media used to conduct the study demonstrate appropriate neutralizing and growth promoting characteristics. To conduct neutralizer effectiveness testing for bacterial recovery, a 2" diameter sample of test substance will be placed in 50 ml of neutralizer (#6) above) and sonicated followed by vortexing. A dilution of the test organism, to deliver ~10-100 Colony Forming Units (CFU)/mL in the final concentration of neutralizer will be added to the jar and mixed thoroughly. A jar of neutralizer without test substance, similarly inoculated, will serve as the positive control. Duplicate 0.5 mL aliquots from the jar will be spread plated on Mac Conkey Agar for the test substances and the positive control. If growth of the test organism on the plates containing test substance, and growth from the positive control are comparable in both number and colonial development, then the neutralizer system is considered adequate. Following incubation, plates will be counted and recorded as CFU/mL. The CFU/sample will then be calculated from this figure. Percent reductions and $Log_{10}$ reductions or increases in the numbers of microorganisms (both types) per sample, as compared to the "Control," will be calculated for each exposure period. The bacterial inhibition property is preferably 40% higher than the untreated pulp, more preferably 50% higher and most preferably 60% higher.

In certain preferred embodiments where the lignocellulosic material is pulp preferably wood pulp, the treated lignocellulosic material of this invention exhibits good wet tensile strength improvement. The exact level of improvement may vary widely, and, in addition to being affected by the level of treatment, is also dependent on the type of fiber furnishes used and the type of sheets made for evaluation. For the unrefined pulp furnishes, while the wet tensile of the control is extremely low, the improvement can be at least about 1.5 or 2 times higher, and preferably can be at least 3-5 times higher than the control as measured by the procedure of Tappi T-456 om-03. For non-Tappi handsheets, such as for tissue and other applications, the level of improvement can vary, depending on refining and wet pressing levels.

In certain preferred embodiments, the treated lignocellulosic material of this invention exhibits good drainage as measured by the procedure of T 221 cm-99.

In certain preferred embodiments, the treated lignocellulosic material of this invention contains bound metal derived from the catalyst. The bound metal is believed to have a beneficial impact on the bactericidal activity of the treated lignocellulosic material. As used herein, "bound" means the metal element that stays with the pulp and is not washed out by pulp washing operations. The nature of the metal binding to the pulp is known to be related to ionic interactions and complex-forming with pulp functional groups such as carbonyl or carboxyl groups as is enhanced by the present invention. The amount of bound metal is determined by the general analytical methods, such as the ICP-Atomic Absorption method and is preferably at least 10 ppm, preferably from about 20 ppm to about 700 ppm, more preferably from about 20 ppm to about 150 ppm and most preferably from about 20 ppm to about 100 ppm.

The treated lignocellulosic material of this invention can be subjected to a number of subsequent processes to further modify the properties of the material. For example, the treated lignocellulosic material can be subsequently treated with a cationic agent which is believed to bind the reducing functional groups of the treated materials. Useful cationic material can vary widely and include cationic nitrogen containing polymers such polyamines, 1-ethyl-3-(3-dimethylaminopropyl)-carbodiimide hydrochloride (EDC), hexadimethrine bromide, polyethyleneimines (bothe linear and branched), copolymers of diallyldimethyl ammonium chloride (DADMAC), copolymers of vinyl pyrrolidone (VP) with quaternized diethylaminoethylmethacrylate (DEAMEMA), polyamides, cationic polyurethane latex, cationic polyvinyl alcohol, polyalkylamines, dicyandiamid copolymers, amine glycigyl addition polymers, poly[oxyethylene (dimethyliminio) ethylene (dimethyliminio) ethylene] dichlorides, high charge-density polyvinylamine, polyallylamine (PAH), poly (hexamethylene biguanide hydrochloride) (i.e. PHMB), polyamidoamine (or polyethylenimine); cationic metal ions, such as water-soluble aluminum salts, calcium salts, and zirconium salts; and these bound ions can act as active complexing sites for sizing and other papermaking chemicals; and cationic dendrimers, such as PAMAM (polyamidoamine) dendrimers with amino surface groups, and polypropylenimine dendrimers with amino surface groups. It is believed that treatment with such cationic materials may modify properties such as increase of paper bulk which is desirable for fine paper, paperboard, tissue, towel, and absorbent products, while maintaining good strength and having decreased water-retention value (WRV) and increased freeness.

Also, the treated lignocellulosic material can be subsequently treated with micro- or nano-particulate metal oxides such as aluminum oxide, titanium oxide, zinc oxide, or silica and are retained by the treated lignocellulosic material to modify properties such as colorant, dye or optical brightener fixation, printability and/or odor control characteristics of the treated lignocellulosic material. The treated lignocellulosic material can be subsequently treated with a cross linking material as for example a water-dispersible or water-soluble bi-, multifunctional carbodiimide and/or polycarbodiimide such as 1,6-hexamethylene bis(ethylcarbodiimide); 1,8-octamethylene bis(ethylcarbodiimide); 1,10 decamethylene bis(ethylcarbodiimide); 1,12 dodecamethylene bis(ethylcarbodiimide); PEG-bis(propyl(ethylcarbodiimide)); 2,2'-dithioethyl bis(ethylcarbodiimde); 1,1'-dithio-p-phenylene bis(ethylcarbodiimide); and 1,1'-dithio-m-phenylene bis(ethylcarbodiimide). during papermaking or fibrous network forming. The bi- or multi-functional carbodiimide groups react with the reducing functional gropes of the material, and cross-linking and locking the fibers of the material inside the paper or fiber network structure.

The treated lignocellulosic material of this invention can be used for conventional purposes in situ or after isolation using conventional product isolation techniques. For example, treated lignocellulosic material of this invention can be used to make paper or paperboard substrates or webs. Methods and apparatuses for preparing a substrate formed of ligno cellulosic fibers are well known in the paper and paperboard art. See for example "Handbook For Pulp & Paper Technologies", $2^{nd}$ Edition, G. A. Smook, Angus Wilde Publications (1992) and references cited therein. Any conventional method and apparatus can be used. Preferably the process comprises: a) providing an aqueous suspension of ligno cellulosic fibers; b) depositing said furnish on a forming wire of a paper making machine to form a wet paper or paperboard web; c) drying the wet paper or paperboard web to obtain dried paper or paperboard web and d) calendering the dried paper or paperboard web. In addition to these process steps, additional process steps known to those of ordinary skill in the art may be employed as for example a coating step to coat one or more surfaces of the dried paper or paperboard web with a coating comprising a binder containing dispersant pigment or treating the dried paper or paperboard at the size press with a sizing agent such as starch.

For example the materials can be used prepared absorbent articles as for example diapers, tissues, towels, personal hygiene products using conventional processes. Such products and their methods of manufacture are known to those of skill in the art and will not be described in detail. See for example, U.S. Pat. Nos. 6,063,982 and 5,766,159 and references described therein. The treated kraft pulp fibers of this invention can be used to make saturating kraft paper. Saturating kraft paper is a paper sheet made from unbleached kraft pulp (mixture of mostly hardwood and some softwood such as southern pine) that is used as substrate for impregnation and curing with resin polymers. Saturating kraft paper is used as home and office building materials, such as kitchen counter tops. A useful property of saturating kraft paper is control the liquid (a polymer resin solution) penetration rate into the sheet, while maintaining paper porosity and density. All of the hardwood kraft fiber in the saturating sheet can be replaced by softwood as for example southern pine kraft (linerboard grade pine kraft) treated by the process of this invention to provide saturating kraft paper having with good liquid transport properties. While we do not wish to be bound by any theory, it is believed that the hemicelluloses carbohydrate layers topochemically located on and inside the kraft fiber are oxidized in the process of this invention increasing the resin liquid absorption into the sheet.

The present invention will be described with references to the following examples. The examples are intended to be illustrative and the invention is not limited to the materials, conditions or process parameters set forth in the examples.

EXAMPLE 1

Bleached Southern Pine Kraft pulp was treated with 1% hydrogen peroxide and 0.03% ferrous sulfate applied on pulp, at a pH 4 and a temperature of 75° C. for 1 hour. The treated pulp was then washed with de-ionized water, and made into paper sheets and dried. The viscosity, copper number and carboxyl number of the treated pulp was determined using the aforementioned procedures. The viscosity of the pulp was 6.2 cp. The copper number of the pulp was 4.5. The carboxyl number of the pulp was 5.5 meq/100 g. The pulp was also evaluated to determine the amount of bound metal. The sample contains 43.4 ppm Fe as bound on the pulp, which is not washed out by water. The bacterial inhibition properties of the pulps were evaluated using the procedure set forth herein above. The bacterial inhibition test results were shown in the table 1 below.

TABLE 1

|  | % E-coli Reduction, 8 hours Vs. Untreated Control pulp | % (E-coli + Ammoniagenes) Reduction, 8 hours Vs. Untreated Control Pulp |
| --- | --- | --- |
| Treated Pulp, 1% peroxide, 0.03% ferrous sulfate | 38% | 23% |

EXAMPLE 2

Bleached Southern Pine Kraft pulp was treated with 1% hydrogen peroxide and 0.03% copper sulfate applied on pulp, at pH 4 and temperature of 80° C. for 1 hour. The viscosity of the pulp was 5.7. The copper number of the pulp was 4.6. The carboxyl number of the pulp was 4.1 meq/100 g. The treated pulp was washed with de-ionized water, and made into paper sheet and dried. The sample contains 90.8 ppm Cu as bound on the pulp.

The pulp was tested for ammonia odor control and bacterial control functions vs. the untreated pulp as control using the procedure described above. The results are shown below in Table 2.

TABLE 2

|  | Metal content in pulp | % E-coli Reduction, 8 hours vs. untreated pulp | % (E-coli + Ammoniagenes) Reduction, 8 hours vs. untreated pulp |
|---|---|---|---|
| Treated Pulp, 1% peroxide, 0.03% copper sulfate | 90.8 ppm Cu | 58% | 68% |
| Treated with 0.03% copper sulfate only | 93 ppm Cu | 44% | 17% |

EXAMPLE 3

Bleached Southern Pine pulp was treated with copper or iron catalyzed hydrogen peroxide oxidation, at pH 4 and 80° C. for 1 hour. The treated pulp was then washed with de-ionized water and made into dry pulp sheets for fiberization by a lab-scale Kamas mill. In this example, 1% and 2% peroxide were used, and catalyst amount was also varied. The pulps were tested for ammonia odor control using the procedure described above. The results are shown below in Table 2.

The results of ammonia odor control were listed in the table 3 below.

TABLE 3

|  | Ammonia gas concentration in headspace, 2 strokes sampling | % NH3 Reduction vs. Untreated pulp | Ammonia gas concentration in headspace, 5 strokes sampling | % NH3 Reduction vs. Untreated pulp | Pulp-bound Trace Metal ppm on pulp |
|---|---|---|---|---|---|
| Untreated Pulp Control | 35.3 ppm NH3 | — | 73.5 ppm NH3 | — | 3 ppm Fe 11 ppm Cu |
| Treated with 1% peroxide, 0.02% copper sulfate | 2.5 ppm NH3 | 93% | 7.3 ppm NH3 | 90% | 43 ppm Cu |
| Treated with 1% peroxide, 0.04% copper sulfate | 2 ppm NH3 | 94% | 4.7 ppm NH3 | 94% | 65 ppm Cu |
| Treated with 2% peroxide, 0.02% copper sulfate | 1 ppm NH3 | 97% | 1.8 ppm NH3 | 98% | 48 ppm Cu |
| Treated with 2% peroxide, 0.04% copper sulfate | 0.7 ppm NH3 | 98% | 1.7 ppm NH3 | 98% | 55 ppm Cu |
| Treated with 1% peroxide, 0.03% ferrous sulfate | 7.1 ppm NH3 | 80% | 14.7 ppm NH3 | 80% | 43 ppm Fe |

EXAMPLE 4

Experiments were conducted applying the metals at 80° C., pH 4 for 1 hour, with both low doses (as in example 3) and very high doses of the metals applied in the absence of the oxidizing agent. The pulps were tested for ammonia odor control vs. the untreated pulp as control using the procedure described above. The results are shown below in Table 4.

TABLE 4

|  | Ammonia gas concentration in the headspace | Pulp-bound Metal ppm on pulp |
|---|---|---|
| Untreated Pulp Control | 35 ppm NH3 | 3 ppm Fe |
| Treated only with 0.03% copper sulfate by our process - washed (No oxidants) | 16 ppm NH3 | 93 ppm Cu |
| Treated only with 0.03% ferrous sulfate by our process - washed (No oxidants) | 14.5 ppm NH3 | 109 ppm Fe |
| Treated only with 0.3% copper sulfate by our process - washed (No oxidants) | 5 ppm NH3 | 283 ppm Cu |
| Treated only with 0.3% ferrous sulfate by our process - washed (No oxidants) | 4 ppm NH3 | 635 ppm Fe |

EXAMPLE 5

Experiments were conducted applying the metals at 80° C., pH 4 for 1 hour. The viscosities of the pulps were determined and the pulps were tested for ammonia odor control vs. the untreated pulp as control using the procedure described above. The results are shown below in Table 5.

TABLE 5

|  | Ammonia gas concentration in the headspace | pH of pulp after washing | Pulp viscosity |
|---|---|---|---|
| Untreated pulp control | 43 ppm NH3 | pH 6.4 | 18 cp |
| Treated with 0.02% zinc sulfate, with 2% peroxide | 41 ppm NH3 | pH 6.3 | 16.7 cp |
| Treated with 0.02% zinc sulfate, 0.01% ferrous sulfate, 2% peroxide | 11 ppm NH3 | pH 6.4 | 4.9 cp |

EXAMPLE 6

This example is to demonstrate the wet strength benefit of a metal-catalyzed peroxide treatment, especially in the preferred pH range of the present invention. Bleached southern pine Kraft pulps were treated with 2% and 3% hydrogen peroxide with 0.03% ferrous sulfate at 80° C. for 1 hour. The pH range was varied from pH 4 to pH 10 at the end of the reaction. Standard 1.2 gram Tappi handsheets were made using the procedure of Tappi T 205 sp-02 and the dry tensile strength, dry tear strength and wet tensile strength were determined using the procedures of Tappi T 494 om-01, Tappi T414 om-01 and Tappi T 456 om-03, respectively. The tensile wet/dry strength values were calculated fro the determined dry tensile strength, dry tear strength and wet tensile strength values. The results were shown in the table 6 below.

TABLE 6

|  | Untreated Pulp, pH 6 | 2% peroxide, end pH 4 | 2% peroxide, 0.2% caustic applied, end pH 4.8 | 2% peroxide, 0.6% caustic applied, end pH 10.3 | 3% peroxide, end pH 4 | 3% peroxide, 0.2% caustic applied, end pH 4.7 | 3% peroxide, 0.6% caustic applied, end ph 10 |
|---|---|---|---|---|---|---|---|
| Dry Tensile, lbs/inch | 9.1 | 10.1 | 12.1 | 13.6 | 9 | 12.9 | 12.5 |
| Dry Tear, gms | 125.5 | 89.7 | 154.3 | 155.1 | 95.3 | 156.3 | 152.8 |
| Wet Tensile, lbs/inch | 0.1 | 0.4 | 0.3 | 0.3 | 0.5 | 0.4 | 0.3 |
| Tensile, Wet/Dry Percent | 1.6 | 4.4 | 2.4 | 1.9 | 5.4 | 2.9 | 2.4 |

EXAMPLE 7

Drying of the treated pulp will decrease the carboxyl groups generated on the fibers. This would not be relevant to the integrated paper/board cases or to the dry fluff pulps and dry forming cases, where the treated pulp would only be dried once. However, it would have an impact on the paper or tissue/towel cases, where the dried treated pulp is purchased, and then re-slushed and made into paper products again by the wet processes and dried again. The results of drying on pulp carboxyl contents are shown in Table 7 below.

TABLE 7

|  | Carboxyl, meq/100 g, Wet Pulp | Carboxyl, meq/100 g, Dried and Rewetted Pulp |
|---|---|---|
| Untreated Bleached Pulp | 3.3 | 3.7 |
| Treated with 2% peroxide, 0.03% ferrous sulfate, at pH 4, 80° C., for 1 hour. | 5.5 | 3.7 |

EXAMPLE 8

Unbleached kraft pulp was used to demonstrate the wet strength improvement on brown pulp as well. The brown high kappa pulp was treated with 2% peroxide, 0.04% ferrous sulfate at pH 4 and 80° C. for an hour. The treated pulp and the untreated pulp control were refined by a Valley beater and made into 300 gsm square hand sheets, wet-pressed and dried on a flatbed dryer. The effect on sheet wet strength is shown in the Table 8 below.

TABLE 8

|  | Pulp freeness | Wet Tensile, lbs/inch |
|---|---|---|
| Untreated Pulp Control | 610 csf | 4.8 |
| Treated with 2% peroxide, 0.04% ferrous sulfate | 625 csf | 10.9 |

EXAMPLE 9

A wet, Southern Pine Kraft pulp was treated with 1% hydrogen peroxide at pH 4 with 0.02% ferrous sulfate applied on pulp. The treatment was done in the mill scale in the bleach plant at 80° C. for 1 hour. In another treatment done in the lab, 3% peroxide was used with 0.04% ferrous sulfate at 80° C. for 2 hours. The treated pulps and the control (production) pulp, without refining, were tested for carbonyl and carboxyl groups. The results were shown in the following Table 9.

TABLE 9

|  | Copper Number | Carboxyl (meq/100 g) |
|---|---|---|
| Control pulp | 0.13 | 4.9 |
| 1% Peroxide mill treated pulp | 4.0 | 5.5 |
| 3% Peroxide lab treated pulp | 6.9 | 7.6 |

As shown in Table 9, 1% peroxide treated pulp has an increase in copper number (30 times higher) and in carboxyl groups (12% higher). A 3% activated peroxide intense treatment resulted in a 52 times higher copper number and 55% increase in carboxyl.

EXAMPLE 10

Mill-dried Market Southern Pine Kraft pulp was re-pulped into pulp slurry. This pulp was treated with 2% hydrogen peroxide at pH 4 with 0.04% ferrous sulfate at a temperature of 80° C. for 1 hour. The copper numbers of the treated and untreated pulp were determined. The results are set forth in the following Table 10.

TABLE 10

|  | Copper Number | Carboxyl (meq/100 g) |
|---|---|---|
| Control Dried Pulp | 0.23 | 3.1 |
| Treated Dried Pulp | 5.6 | 4.1 |

The results set forth in Table 10 indicate, the treated pulp has 23 times higher Copper number, and an increase of carboxyl by 32% as compared to the untreated pulp control.

EXAMPLE 11

The pulp slurry as in Example 11 was treated with 1% hydrogen peroxide with 0.02% ferrous sulfate, at pH 4, 80° C.

for 1 hour. The copper number was increased from 0.23 to 5.3. Both the treated pulp and the control pulps were further treated high charge density polyvinylamine and were formed into Tappi hand sheets were made using the procedure of Tappi T 205 sp-02. The basis weight and caliper of the handsheets were determined by the procedures of Tappi T 410 om-02 and Tappi T 411 om-05, respectively and the bulk of control and treated pulps were calculated from the basis weight and caliper. The results are set forth in the following Table 11.

TABLE 11

|  | Control Pulp | Control Pulp + 0.2% polyvinylainine | Treated Pulp | Treated Pulp + 0.24% polyvinylamine |
|---|---|---|---|---|
| Bulk, cc/g | 1.79 | 1.84 | 1.83 | 1.91 |

EXAMPLE 12

A wet, bleached Southern Pine Kraft pulp was treated with 1% hydrogen peroxide and 0.02% ferrous sulfate at pH4 for 1 hour at 80° C. Both the treated pulp and the control pulp were made into Williams hand sheets. The dried hand sheets were then fluffed by a lab-scale Kamas mill. The liquid absorption capacity was tested (SCAN method). The results are set forth in the following Table 12.

TABLE 12

|  | Control Pulp | Treated Pulp |
|---|---|---|
| SCAN Liquid Absorption Capacity, g/g | 8.9 | 9.6 |

From the results shown in Table 12, it is clear that the treated pulp has better liquid absorption capacity than the control pulp. In fact, this enhanced liquid absorption capacity, combined with the enhanced southern pine fiber collapsibility due to our activated peroxide treatment, makes this treated southern pine pulp quite valuable in some hygiene products where super absorbent particles (SAP) are not used.

EXAMPLE 13

"Mercerized Kraft Pulp" was formed by treating Southern Pine kraft pulp with a caustic solution (10% concentration) for 5 minutes at a temperature of 40° C. The "mercerized pulp" was with 1% hydrogen peroxide in the presence of 0.02% ferrous sulfate at pH 4 and 80° C. for 1 hour. The freeness treated and untreated mercerized pulp was evaluated by the procedure of Tappi T 227 om-99 and average fiber length of treated and untreated mercerized pulp was determined by a Kajanni. The treated and untreated mercerized pulp was formed into Tappi Hand sheets using the procedure of Tappi T 205 sp-02 and the basis weight and internal bond of the hand sheets were determined by the procedures of Tappi T 410 om-02 and Tappi T 569 om-00, respectively. The bulk was calculated from the caliper and basis weight as described above. The results bare set forth in the following Table 13.

TABLE 13

|  | Freeness, CSF | Basis Weight, g/m2 | Bulk, cc/g | Internal Bond, ft-lb/1000 sq ft | Average. Fiber Length, L(L), mm |
|---|---|---|---|---|---|
| Mercerized Southern Pine Kraft | 730 | 160.3 | 2.75 | 20 | 2.04 |
| Mercerized post-treated with 1% activated peroxide | 740 | 154.8 | 3.55 | 19 | 1.9 |
| Untreated Southern Pine Kraft | 740 |  |  |  | 2.53 |

EXAMPLE 14

An oxygen delignified Southern Pine Kraft pulp was treated with a cellulose enzyme (Multifect A40 from Genencor) at a dose of 0.2% on pulp. This enzyme treated pulp was further treated with 1.5% hydrogen peroxide with 0.02% ferrous sulfate at pH 4 and temperature of 80° C. for 1 hour. The freeness and average fiber length of treated and untreated mercerized pulp were determined by the procedures used above in the examples. The treated and untreated pulps were formed into a fibrous web and the web fluff shredded using Kamas lab scale hammermill. The fluff shredding energy determined. The results are shown in Table 14.

TABLE 14

|  | Freeness, CSF | Average FQA Fiber Length, L(L), mm | Fluff Shredding Energy, KJ/kg |
|---|---|---|---|
| Untreated Southern Pine | 743 | 2.68 | 223 |
| Enzyme Treated | 740 | 2.6 2.13 | — |
| Enzyme-treated, then post-treated with 1.5% activated peroxide | 740 607 470 | 2.61 1.26 1.07 | 201 |

EXAMPLE 15

Linerboard grade southern pine Kraft (kappa 110) that 2% activated peroxide treatment of a low-cost with 0.04% ferrous sulfate at pH4 and 1 hour at a temperature of 80° C. The freeness of the treated pulp was determined using the procedure described in the above examples. For comparison purposes the freeness of a mixture of 80% untreated hardwood/20% untreated southern pine was also evaluated. Tappi hand sheets formed from 100% treated southern pine and formed from a mixture of 80% untreated hardwood/20% untreated southern pine were evaluated to determine Gurley Porosity (Tappi T 536 om-02) and the average PHST (Tappi T 530 om-02 with a phenolic resin liquid), respectively. The results are set forth in the following table 15.

TABLE 15

|  | 80% Hardwood/ 20% Pine | 100% Treated Pine |
|---|---|---|
| Freeness, CSF | 600 | 682 (fiber length 2.3 mm) |
| Density | 11.9 | 12.5 |
| Gurley Porosity | 22.1 | 22.9 |
| Ave. PHST, seconds | 60 per side | 29 per side |

The data in table 15 shows that treated southern pine pulp can be used to replace all the low-yield hardwood in saturating kraft paper.

EXAMPLE 16

A bleached Southern Pine Kraft pulp was mixed with 2% hydrogen peroxide with 0.02% ferrous sulfate at pH 4, pH 7, and pH 12 respectively. The pulps at 1% consistency were under constant stirring at room temperature. A quartz plate was placed on top of the pulp slurry. A bench-top PS2 Ultra-violet device (medium pressure mercury lamp) was used to irradiate the pulp slurry through the quartz plate. Fifteen minutes of UV irradiation were used in these treatments. After UV irradiation, no peroxide residuals were detected. The pulp temperature was not increased by the treatment. The pulp viscosity was 3.2 cp for pH 4, 3.9 cp for pH 7, and 10.6 cp for pH 10. The pulp treated at pH 7 has a copper number of 6.2.

EXAMPLE 18

A bleached southern pine Kraft pulp was treated with iron, copper, or combined Fe/Cu catalysts with hydrogen peroxide, at pH 4 and 80° C. for 1.5 hours. The treated pulp and the control pulp were washed to pH 6 and made into dry sheets. The dry sheets were then fluffed by the Hammermill as described previously and were tested for ammonia adsorption. The results of ammonia absorption were shown in the following table 17 below.

TABLE 17

|  | Pulp Viscosity, cp. | Ammonia gas concentration in headspace | % Ammonia reduction |
|---|---|---|---|
| Untreated Control Pulp | 21.4 | 300 ppm NH3 | — |
| Treated with 1% peroxide, 0.03% ferrous sulfate | 4.5 | 50 ppm NH3 | 83% |
| Treated with 2% peroxide, 0.03% ferrous sulfate | 3.9 | 26 ppm NH3 | 91% |
| Treated with 3% peroxide, 0.04% ferrous sulfate | 3.2 | 11 ppm NH3 | 96% |
| Treated with 1% peroxide, 0.04% copper sulfate | 9.7 | 130 ppm NH3 | 57% |
| Treated with 1% peroxide, 0.04% copper sulfate | 7.2 | 105 ppm NH3 | 64%) |
| Treated with 2% peroxide, 0.04% copper sulfate | 5.7 | 41 ppm NH3 | 86% |
| Treated with 2% peroxide, 0.04% copper sulfate | 5.5 | 48 ppm NH3 | 84% |
| Treated with 2% peroxide, 0.02% copper sulfate | 8.9 | 80 ppm NH3 | 73% |
| Treated with 2% peroxide, 0.02% copper sulfate | 6.5 | 75 ppm NH3 | 74% |
| Treated with 2% peroxide, 0.03% ferrous sulfate, 0.02% copper sulfate | 3.2 | 15 ppm NH3 | 95% |

Finally, variations from the examples given herein are possible in view of the above-disclosure. Therefore, although the invention has been described with reference to certain preferred embodiments, it will be appreciated that other compositions may be devised, which are nevertheless within the scope and spirit of the invention as defined in the claims appended hereto. The foregoing description of various and preferred embodiments of the present invention has been provided for purposes of illustration only, and it is understood that numerous modifications, variations and alterations may be made thereto without departing from the spirit or scope of the invention as set forth in the following claims.

What is claimed is:

1. A personal hygiene article for absorbing fluids, the article comprising: at least one fluid permeable top sheet layer and at least one substantially fluid impermeable back sheet layer; and an absorbent sub layer material interposed between the top sheet layer and the back sheet layer, the sub layer material comprising a treated bleached Kraft pulp; said treated bleached Kraft pulp made by a process comprising treating a Kraft pulp with a at least one transition metal catalyst in the presence of an at least one oxidizing agent selected from the group consisting of hydrogen peroxide, chlorine dioxide, hypochlorite, and hypochlorous acid at a pH ranging from 1 to 9, wherein the treated bleached Kraft pulp has a viscosity of equal to or less than about 10 cps.

2. The personal hygiene article for absorbing fluids according to claim 1, wherein the treated bleached Kraft pulp has a copper number equal to or greater than about 3.

3. The personal hygiene article for absorbing fluids according to claim 1, wherein the treated bleached Kraft pulp has a copper number equal to or greater than about 4.4.

4. The personal hygiene article for absorbing fluids according to claim 1, wherein the treated bleached Kraft pulp has a copper number equal to or greater than about 5.

5. The personal hygiene article for absorbing fluids according to claim 1, wherein the treated bleached Kraft pulp has a copper number equal to or greater than about 5.5.

6. The personal hygiene article for absorbing fluids according to claim 1, wherein the treated bleached Kraft pulp has a carboxy number equal to or more than about 3.5 meq/100 grams of oven dried treated pulp.

7. The personal hygiene article for absorbing fluids according to claim 1, wherein the treated bleached Kraft pulp has a carboxy number equal to or more than about 4 meq/100 grams of oven dried treated pulp.

8. The personal hygiene article for absorbing fluids according to claim 1, wherein the treated treated bleached Kraft pulp has a carboxy number equal to or more than about 5 meq/100 grams of oven dried treated pulp.

9. The personal hygiene article for absorbing fluids according to claim 1, wherein the treated treated bleached Kraft pulp has a carboxy number equal to or more than about 5.5 meq/100 grams of oven dried treated pulp.

10. The personal hygiene article for absorbing fluids according to claim 1, wherein the at least one transition metal catalyst comprises at least one of copper and iron.

11. The personal hygiene article for absorbing fluids according to claim 1, wherein the at least one oxidizing agent is hydrogen peroxide.

12. The personal hygiene article for absorbing fluids according to claim 1, wherein said treated bleached Kraft pulp is made by a process comprising treating a Kraft pulp with the at least one transition metal catalyst in the presence of an oxidizing agent at pH of from 2 to 6.

13. The personal hygiene article for absorbing fluids according to claim 1, wherein the at least one transition metal catalyst comprises iron.

14. The personal hygiene article for absorbing fluids according to claim 1, wherein the treated bleached Kraft pulp has a viscosity of from about 1 to about 10 cps.

15. The personal hygiene article for absorbing fluids according to claim 1, wherein the treated bleached Kraft pulp has a viscosity of from about 2 to about 7 cps.

\* \* \* \* \*